US009668817B2

(12) United States Patent
Anderson et al.

(10) Patent No.: US 9,668,817 B2
(45) Date of Patent: Jun. 6, 2017

(54) PRESSURE WIRE DETECTION AND COMMUNICATION PROTOCOL FOR USE WITH MEDICAL MEASUREMENT SYSTEMS

(71) Applicant: Volcano Corporation, San Diego, CA (US)

(72) Inventors: David Anderson, Temecula, CA (US); Douglas E. Meyer, Folsom, CA (US)

(73) Assignee: Volcano Corporation, San Diego, CA (US)

( * ) Notice: Subject to any disclaimer, the term of this patent is extended or adjusted under 35 U.S.C. 154(b) by 580 days.

(21) Appl. No.: 14/212,605

(22) Filed: Mar. 14, 2014

(65) Prior Publication Data

US 2014/0266577 A1 Sep. 18, 2014

Related U.S. Application Data

(60) Provisional application No. 61/788,355, filed on Mar. 15, 2013.

(51) Int. Cl.
*H04L 9/32* (2006.01)
*A61B 8/00* (2006.01)
(Continued)

(52) U.S. Cl.
CPC ............... *A61B 19/44* (2013.01); *A61B 5/02* (2013.01); *A61B 5/026* (2013.01); *A61B 5/0215* (2013.01);
(Continued)

(58) Field of Classification Search
CPC ...................................................... A61B 2/15
See application file for complete search history.

(56) References Cited

U.S. PATENT DOCUMENTS 5,746,495 A * 5/1998 Klamm ............... F21L 4/04
362/183
2003/0004403 A1 1/2003 Drinan
(Continued)

FOREIGN PATENT DOCUMENTS

| JP | 2011-221784 A | 11/2011 |
|----|---------------|---------|
| WO | 2010151246 A1 | 12/2010 |
| WO | 2012155040 A1 | 11/2012 |

OTHER PUBLICATIONS

International Search Report and Written Opinion received in Patent Cooperation Treaty Application No. PCT/US2014/026593, dated Jul. 3, 2014, 10 pages.

*Primary Examiner* — Joseph Feild
*Assistant Examiner* — Pameshanand Mahase

(57) ABSTRACT

One aspect of the present disclosure involves a method. The method includes retrieving, from a diagnostic medical device, identification information that identifies a feature of the diagnostic medical device. A proprietary signal is generated in response to the identification information. The proprietary signal is sent to a medical measurement system to facilitate an unlocking of one or more programs to be executed on the medical measurement system. Another aspect of the present disclosure involves a method. The method includes detecting, through an electronic interface device, a coupling of a remote diagnostic medical device. Thereafter, a proprietary signal is received from the electronic interface device. An identity feature of the remote diagnostic medical device is ascertained based on the proprietary signal. One or more programs are unlocked for execution if the identity feature of the remote diagnostic medical device matches a predetermined identity feature.

23 Claims, 9 Drawing Sheets

(51) Int. Cl.
  *A61B 5/02* (2006.01)
  *A61B 5/05* (2006.01)
  *A61B 19/00* (2006.01)
  *A61B 5/00* (2006.01)
  *A61B 5/0215* (2006.01)
  *A61B 5/026* (2006.01)
  *A61B 90/90* (2016.01)
  *A61B 90/98* (2016.01)
  *G06F 21/44* (2013.01)

(52) U.S. Cl.
  CPC ............ *A61B 5/6851* (2013.01); *A61B 90/90* (2016.02); *A61B 90/98* (2016.02); *G06F 21/44* (2013.01); *A61B 2560/0266* (2013.01); *A61B 2562/08* (2013.01); *A61B 2562/226* (2013.01)

(56) References Cited

U.S. PATENT DOCUMENTS

| | | | |
|---|---|---|---|
| 2006/0100618 A1* | 5/2006 | Chan | A61B 18/1492 606/41 |
| 2006/0156415 A1* | 7/2006 | Rubinstein | G06F 21/445 726/27 |
| 2006/0247606 A1 | 11/2006 | Batch | |
| 2008/0061153 A1* | 3/2008 | Hickle | A61M 16/183 235/492 |
| 2010/0045425 A1 | 2/2010 | Chivallier | |
| 2010/0280330 A1 | 11/2010 | Samuelsson | |
| 2012/0245438 A1 | 9/2012 | Bernini | |
| 2012/0271178 A1 | 10/2012 | Smith | |
| 2013/0046190 A1* | 2/2013 | Davies | A61B 5/0215 600/486 |
| 2013/0304061 A1* | 11/2013 | Chang | A61B 18/1492 606/41 |

\* cited by examiner

PRESSURE WIRE DETECTION AND COMMUNICATION PROTOCOL FOR USE WITH MEDICAL MEASUREMENT SYSTEMS

CROSS-REFERENCE TO RELATED APPLICATIONS

The present application claims priority to and the benefit of U.S. Provisional Patent Application No. 61/788,355, filed Mar. 15, 2013, which is hereby incorporated by reference in its entirety.

TECHNICAL FIELD

The present disclosure relates generally to the detection of a diagnostic medical device, and in particular, to the detection of a proprietary diagnostic medical device and unlocking of certain functionalities on a medical measurement system in response to the detection.

BACKGROUND

In the modern day healthcare industry, measurement instruments or systems may be utilized in combination with remote diagnostic medical devices to obtain sensitive medical measurement data. For example, a hemodynamic system may work in conjunction with a pressure guide wire to make proximal or aortic pressure measurements for a patient. It is desirable for a manufacturer of a diagnostic medical device (such as the pressure guide wire) to have the output of its sensors available to a medical measurement system for further analysis and display to a user. However, certain analytic programs within the medical measurement system may be intended for exclusive use with the output of a particular manufacturer's medical devices. For some applications, the necessary sensor data may vary between manufacturers with the potential for inaccurate analysis. Therefore, in order to ensure patient safety and to provide accurate analytic results, there remains a need for the manufacturers of diagnostic medical devices to control access to proprietary analytic tools on medical measurement systems.

SUMMARY

One aspect of the present disclosure involves a method. The method includes retrieving, from a diagnostic medical device, identification information that identifies a feature of the diagnostic medical device; generating a proprietary signal in response to the identification information; and sending the proprietary signal to a medical measurement system to facilitate an unlocking of one or more programs to be executed on the medical measurement system.

Another one aspect of the present disclosure involves a method. The method includes: detecting, through an electronic interface device, a coupling of a remote diagnostic medical device; receiving, from the electronic interface device, a proprietary signal; ascertaining an identity feature of the remote diagnostic medical device based on the proprietary signal; and unlocking one or more programs for execution if the identity feature of the remote diagnostic medical device matches a predetermined identity feature.

One more aspect of the present disclosure involves a method. The method includes: coupling a diagnostic medical device to a medical measurement system; causing a proprietary signal to be sent to the medical measurement system; receiving, from the medical measurement system, confirmation that an identity feature of the diagnostic medical device has been ascertained, based on the proprietary signal, to match a predetermined identity feature; and causing an execution of one or more programs that have been unlocked on the medical measurement system in response to the confirmation.

Yet another aspect of the present disclosure involves a system. The system includes: a diagnostic medical device configured to contain identification information that identifies a feature of the diagnostic medical device; and an electronic interface device configured to serve as an interface between the diagnostic medical device and a medical measurement system; wherein the electronic interface device is configured to generate, in response to the identification information, a proprietary signal that facilitates an unlocking of one or more programs for execution on the medical measurement system.

Yet one more aspect of the present disclosure involves a method. The method includes: detecting an attempted execution of a program; querying one of: an electronic interface device or a remote diagnostic medical device regarding identification information of the diagnostic medical device; determining whether the identification information of the diagnostic medical device matches predefined identification information; and unlocking the program for execution if the identification information of the diagnostic medical device matches the predefined identification information.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
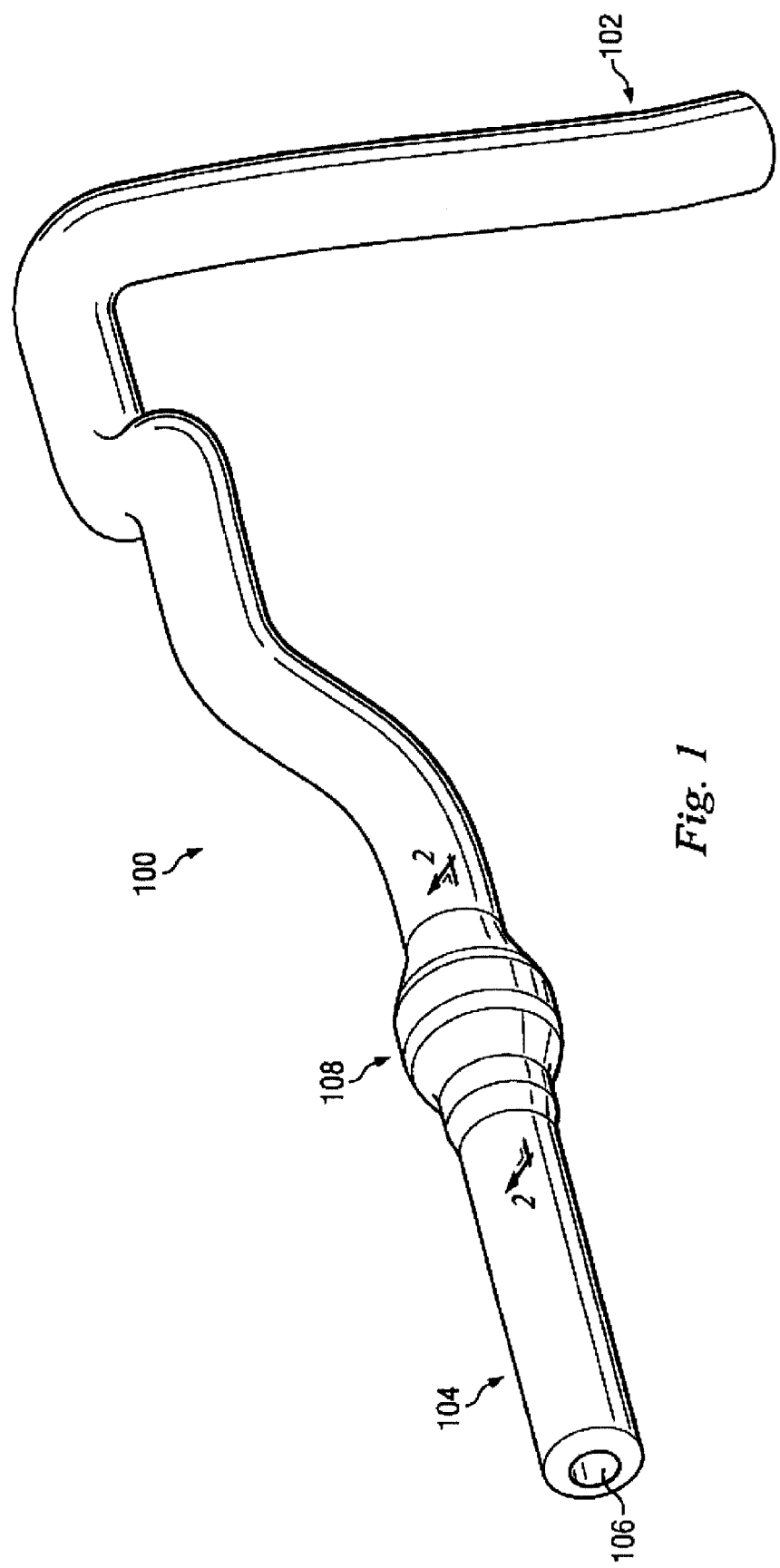
FIG. 1 is a diagrammatic perspective view of a vessel having a stenosis according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Over the years, certain medical device manufacturers have developed proprietary programs that can be executed on the medical measurement systems for better analysis of the medical measurement data. For example, a fractional flow reserve (FFR) measurement may be developed as proprietary programs for assessing the severity of a stenosis in a blood vessel. In more detail, FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment. Common treatment options include angioplasty and stenting.

Coronary blood flow is unique in that it is affected not only by fluctuations in the pressure arising proximally (as in the aorta) but is also simultaneously affected by fluctuations arising distally in the microcirculation. Accordingly, it is not possible to accurately assess the severity of a coronary stenosis by simply measuring the fall in mean or peak pressure across the stenosis, because the distal coronary pressure is not purely a residual of the pressure transmitted from the aortic end of the vessel. As a result, for an effective calculation of FFR within the coronary arteries, it is necessary to reduce the vascular resistance within the vessel. Currently, pharmacological hyperemic agents, such as adenosine, are administered to reduce and stabilize the resistance within the coronary arteries. These potent vasodilator agents reduce the dramatic fluctuation in resistance (predominantly by reducing the microcirculation resistance associated with the systolic portion of the heart cycle) to obtain a relatively stable and minimal resistance value.

However, the administration of hyperemic agents is not always possible or advisable. First, the clinical effort of administering hyperemic agents can be significant. In some countries (particularly the United States), hyperemic agents such as adenosine are expensive, and time consuming to obtain when delivered intravenously (IV). In that regard, IV-delivered adenosine is generally mixed on a case-by-case basis in the hospital pharmacy. It can take a significant amount of time and effort to get the adenosine prepared and delivered to the operating area. These logistic hurdles can impact a physician's decision to use FFR. Second, some patients have contraindications to the use of hyperemic agents such as asthma, severe COPD, hypotension, bradycardia, low cardiac ejection fraction, recent myocardial infarction, and/or other factors that prevent the administration of hyperemic agents. Third, many patients find the administration of hyperemic agents to be uncomfortable, which is only compounded by the fact that the hyperemic agent may need to be applied multiple times during the course of a procedure to obtain FFR measurements. Fourth, the administration of a hyperemic agent may also require central venous access (e.g., a central venous sheath) that might otherwise be avoided. Finally, not all patients respond as expected to hyperemic agents and, in some instances, it is difficult to identify these patients before administration of the hyperemic agent.

To address the various problems discussed above with the administration hyperemic agents, another proprietary measurement technique, known as an instantaneous wave-free ratio (iFR) measurement, has been developed. An iFR measurement accomplishes similar tasks as an FFR measurement without the need to administer the hyperemic agents. A more in depth discussion of FFR and iFR may be found in Provisional U.S. Patent Application No. 61/588,437, filed on Jan. 19, 2012, and entitled "Interface Devices, Systems, and Methods for Use with Intravascular Pressure Monitoring Devices", and U.S. patent application Ser. No. 13/460,296, filed on Apr. 30, 2012, and entitled "Devices, Systems, and Methods for Assessing a Vessel", the disclosures of each of which are hereby incorporated by reference in their entirety.

It can be seen that proprietary programs enhance the functionality and capability of the medical measurement systems on which they are executed. However, a medical device manufacturer who is also the developer of these proprietary programs may wish to make these programs available only on medical measurement systems that are coupled with diagnostic medical devices made by the medical device manufacturer. One reason for the limited access of the proprietary programs pertains to measurement and analytic accuracy. Though other medical device manufacturers make produce diagnostic medical devices that are somewhat compatible with a medical measurement system, one cannot be certain of the measurement results delivered by these other diagnostic medical devices. If these measurement results are inaccurate, they may cause the proprietary programs to produce inaccurate analyses. Another reason for the limited access of the proprietary programs pertains to patient safety. Again, if the proprietary programs produce inaccurate analytic results based on the inaccurate measurements made by diagnostic medical devices from other manufacturers, the safety of the patient may be compromised. For example, a patient who has a discoverable health risk (if accurate diagnostic medical tools are used) may now be misdiagnosed as being healthy. If the patient suffers a health setback or dies due to the misdiagnosis, the medical device manufacturer (who is the developer of the proprietary programs) may be found liable, even though its diagnostic medical tools were not used in making the diagnosis.

Based on these reasons discussed above, a medical device manufacturer who is also the developer of these proprietary programs has good reasons to make these proprietary programs conditionally available only if its brand of diagnostic medical devices are deployed in conjunction with the medical measurement systems. For example, a manufacturer of diagnostic medical devices (e.g., pressure guide wires) may make proprietary programs such as FFR and iFR available only if its brand of pressure guide wires are detected. It is understood that in some embodiments, the proprietary programs such as iFR are installed on the medical measurement system of a third party (i.e., a different manufacturer of medical measurement systems), but these programs are designed to work only with a specific manufacturer of diagnostic devices. For example, a manufacturer X of a diagnostic device may develop the proprietary programs as software. A different manufacturer Y manufactures a medical measurement system that communicates with the diagnostic device. The manufacturer X may license the necessary software to manufacturer Y, so that the software containing the proprietary programs may be executed on the medical measurement systems made by the manufacturer Y. However, according to the present disclosure, these proprietary programs will be executed only if a correct identification feature of the diagnostic device has been verified. For example, the identification feature may include the identity of the manufacturer (e.g., made by the manufacturer X), a manufacturing site, an expiration date, date of past use, etc. An example scenario according to the various aspects of the present disclosure is discussed in more detail below with reference to FIGS. 1-8.

Figure 2:
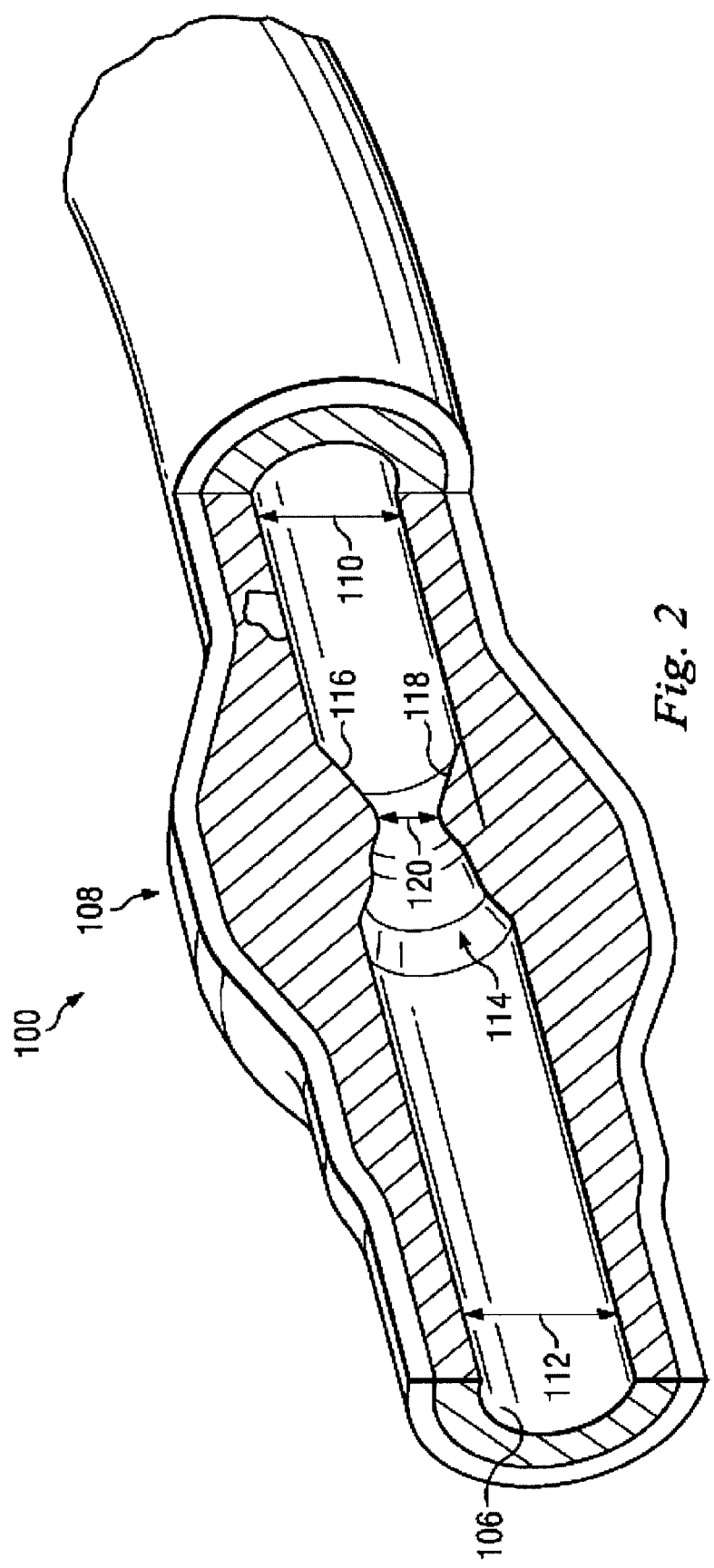
FIG. 2 is a diagrammatic, partial cross-sectional perspective view of a portion of the vessel of FIG. 1 taken along section line 2-2 of FIG. 1.

Referring to FIGS. 1 and 2, shown therein is a vessel 100 having a stenosis according to an embodiment of the present disclosure. In that regard, FIG. 1 is a diagrammatic perspective view of the vessel 100, while FIG. 2 is a partial cross-sectional perspective view of a portion of the vessel 100 taken along section line 2-2 of FIG. 1. Referring more specifically to FIG. 1, the vessel 100 includes a proximal portion 102 and a distal portion 104. A lumen 106 extends along the length of the vessel 100 between the proximal portion 102 and the distal portion 104. In that regard, the lumen 106 is configured to allow the flow of fluid through the vessel. In some instances, the vessel 100 is a blood vessel. In some particular instances, the vessel 100 is a coronary artery. In such instances, the lumen 106 is configured to facilitate the flow of blood through the vessel 100.

As shown, the vessel 100 includes a stenosis 108 between the proximal portion 102 and the distal portion 104. Stenosis 108 is generally representative of any blockage or other structural arrangement that results in a restriction to the flow of fluid through the lumen 106 of the vessel 100. Embodiments of the present disclosure are suitable for use in a wide variety of vascular applications, including without limitation coronary, peripheral (including but not limited to lower limb, carotid, and neurovascular), renal, and/or venous. Where the vessel 100 is a blood vessel, the stenosis 108 may be a result of plaque buildup, including without limitation plaque components such as fibrous, fibro-lipidic (fibro fatty), necrotic core, calcified (dense calcium), blood, fresh thrombus, and mature thrombus. Generally, the composition of the stenosis will depend on the type of vessel being evaluated. In that regard, it is understood that the concepts of the present disclosure are applicable to virtually any type of blockage or other narrowing of a vessel that results in decreased fluid flow.

Referring more particularly to FIG. 2, the lumen 106 of the vessel 100 has a diameter 110 proximal of the stenosis 108 and a diameter 112 distal of the stenosis. In some instances, the diameters 110 and 112 are substantially equal to one another. In that regard, the diameters 110 and 112 are intended to represent healthy portions, or at least healthier portions, of the lumen 106 in comparison to stenosis 108. Accordingly, these healthier portions of the lumen 106 are illustrated as having a substantially constant cylindrical profile and, as a result, the height or width of the lumen has been referred to as a diameter. However, it is understood that in many instances these portions of the lumen 106 will also have plaque buildup, a non-symmetric profile, and/or other irregularities, but to a lesser extent than stenosis 108 and, therefore, will not have a cylindrical profile. In such instances, the diameters 110 and 112 are understood to be representative of a relative size or cross-sectional area of the lumen and do not imply a circular cross-sectional profile.

As shown in FIG. 2, stenosis 108 includes plaque buildup 114 that narrows the lumen 106 of the vessel 100. In some instances, the plaque buildup 114 does not have a uniform or symmetrical profile, making angiographic evaluation of such a stenosis unreliable. In the illustrated embodiment, the plaque buildup 114 includes an upper portion 116 and an opposing lower portion 118. In that regard, the lower portion 118 has an increased thickness relative to the upper portion 116 that results in a non-symmetrical and non-uniform profile relative to the portions of the lumen proximal and distal of the stenosis 108. As shown, the plaque buildup 114 decreases the available space for fluid to flow through the lumen 106. In particular, the cross-sectional area of the lumen 106 is decreased by the plaque buildup 114. At the narrowest point between the upper and lower portions 116, 118 the lumen 106 has a height 120, which is representative of a reduced size or cross-sectional area relative to the diameters 110 and 112 proximal and distal of the stenosis 108. Note that the stenosis 108, including plaque buildup 114 is exemplary in nature and should be considered limiting in any way. In that regard, it is understood that the stenosis 108 has other shapes and/or compositions that limit the flow of fluid through the lumen 106 in other instances. While the vessel 100 is illustrated in FIGS. 1 and 2 as having a single stenosis 108 and the description of the embodiments below is primarily made in the context of a single stenosis, it is nevertheless understood that the devices, systems, and methods described herein have similar application for a vessel having multiple stenosis regions.

Figure 3:
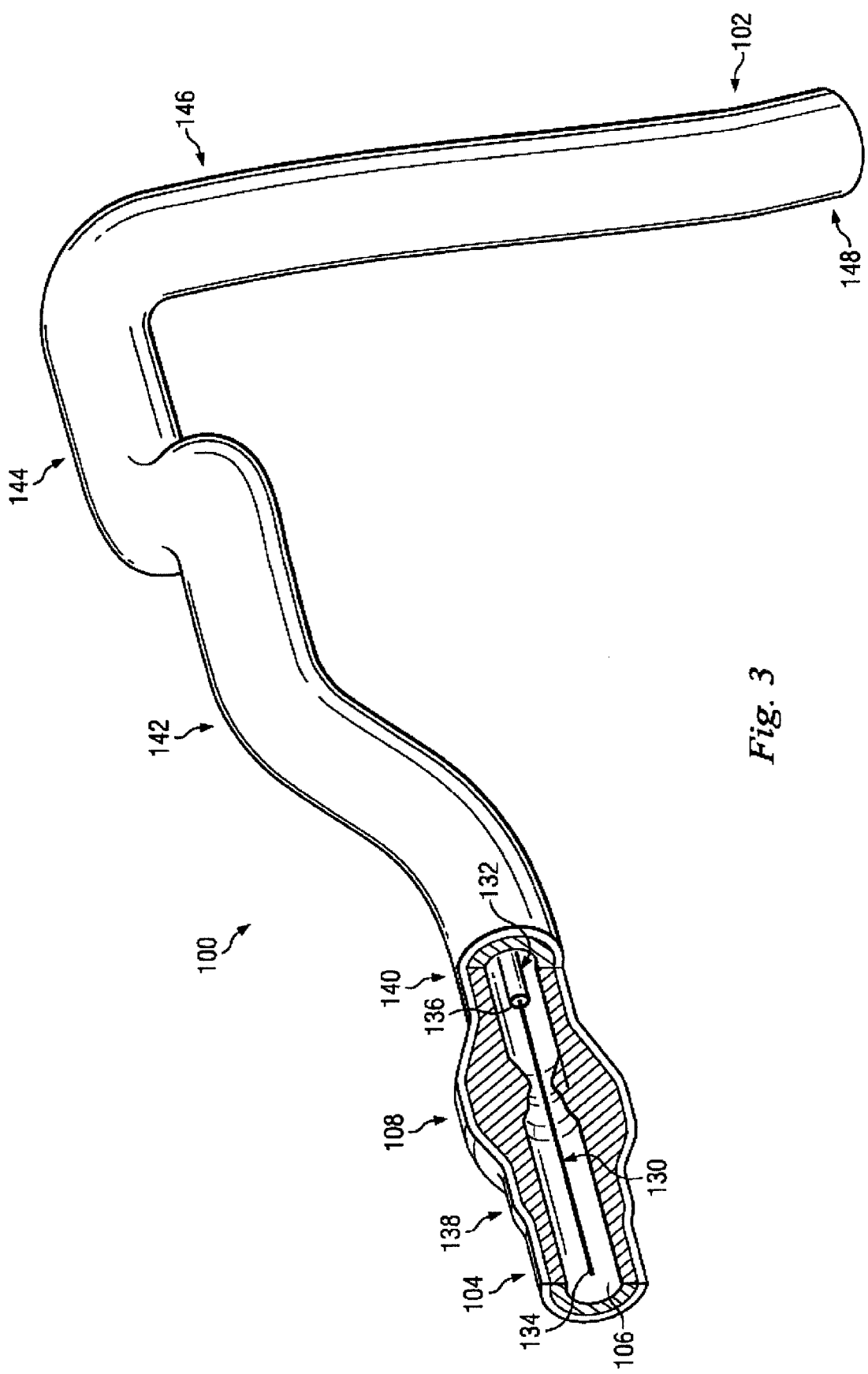
FIG. 3 is a diagrammatic, partial cross-sectional perspective view of the vessel of FIGS. 1 and 2 with instruments positioned therein according to an embodiment of the present disclosure.

Referring now to FIG. 3, the vessel 100 is shown with instruments 130 and 132 positioned therein according to an embodiment of the present disclosure. In general, instruments 130 and 132 may be any form of device, instrument, or probe sized and shaped to be positioned within a vessel. In the illustrated embodiment, instrument 130 is generally representative of a guide wire, while instrument 132 is generally representative of a catheter. In that regard, instrument 130 extends through a central lumen of instrument 132. However, in other embodiments, the instruments 130 and 132 take other forms. In that regard, the instruments 130 and 132 are of similar form in some embodiments. For example, in some instances, both instruments 130 and 132 are guide wires. In other instances, both instruments 130 and 132 are catheters. On the other hand, the instruments 130 and 132 are of different form in some embodiments, such as the illustrated embodiment, where one of the instruments is a catheter and the other is a guide wire. Further, in some instances, the instruments 130 and 132 are disposed coaxial with one another, as shown in the illustrated embodiment of FIG. 3. In other instances, one of the instruments extends through an off-center lumen of the other instrument. In yet other instances, the instruments 130 and 132 extend side-by-side. In some particular embodiments, at least one of the instruments is as a rapid-exchange device, such as a rapid-exchange catheter. In such embodiments, the other instrument is a buddy wire or other device configured to facilitate the introduction and removal of the rapid-exchange device. Further still, in other instances, instead of two separate instruments 130 and 132 a single instrument is utilized. In that regard, the single instrument incorporates aspects of the functionalities (e.g., data acquisition) of both instruments 130 and 132 in some embodiments.

Instrument 130 is configured to obtain diagnostic information about the vessel 100. In that regard, the instrument 130 is a diagnostic medical device that includes one or more sensors, transducers, and/or other monitoring elements configured to obtain the diagnostic information about the vessel. The diagnostic information obtained by the diagnostic medical device includes one or more of the following: pressure, flow (velocity), images (including images obtained using ultrasound (e.g., IVUS), OCT, thermal, and/or other imaging techniques), temperature, and/or combinations thereof. The one or more sensors, transducers, and/or other monitoring elements are positioned adjacent a distal portion of the instrument 130 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 134 of the instrument 130 in some instances. In some instances, at least one of the one or more sensors, transducers, and/or other monitoring elements is positioned at the distal tip of the instrument 130.

The instrument 130 includes at least one element configured to monitor a medical parameter within the vessel 100. In the illustrated embodiment, blood pressure is the medical parameter being monitored, though other medical parameters such as flow may be monitored in different embodiments. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. Examples of commercially available guide wire products that include suitable pressure monitoring elements include, without limitation, the PrimeWire Prestige® PLUS pressure guide wire, the PrimeWire PRESTIGE® pressure guide wire, the PrimeWire® pressure guide wire, and the ComboWire® XT pressure and flow guide wire, each available from Volcano Corporation. Generally, the instrument 130 is sized such that it can be positioned through the stenosis 108 without significantly impacting fluid flow across the stenosis, which would impact the distal pressure reading. Accordingly, in some instances the instrument 130 has an outer diameter of 0.035" or less. In some embodiments, the instrument 130 has an outer diameter of 0.018" or less. In some other embodiments, the instrument 130 has an outer diameter of 0.014" or less.

Instrument 132 is also configured to obtain diagnostic information about the vessel 100. In some instances, instrument 132 is configured to obtain the same diagnostic information as instrument 130. In other instances, instrument 132 is configured to obtain different diagnostic information than instrument 130, which may include additional diagnostic information, less diagnostic information, and/or alternative diagnostic information. The diagnostic information obtained by instrument 132 includes one or more of pressure, flow (velocity), images (including images obtained using ultrasound (e.g., IVUS), OCT, thermal, and/or other imaging techniques), temperature, and/or combinations thereof. Instrument 132 includes one or more sensors, transducers, and/or other monitoring elements configured to obtain this diagnostic information. In that regard, the one or more sensors, transducers, and/or other monitoring elements are positioned adjacent a distal portion of the instrument 132 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 136 of the instrument 132 in some instances. In some instances, at least one of the one or more sensors, transducers, and/or other monitoring elements is positioned at the distal tip of the instrument 132.

Similar to instrument 130, instrument 132 also includes at least one element configured to monitor a medical parameter within the vessel 100. In the illustrated embodiment, blood pressure is the medical parameter being monitored, though other medical parameters such as flow may be monitored in different embodiments. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. In this example, the instrument 132 may include a fluid pressure transducer, which would be attached to a guide catheter or manifold. Such transducer is compatible with the following hemodynamic monitoring systems: Siemens AXIOM Sensis, Mennen Horizon XVu, and Philips Xper IM Physiomonitoring 5.

In accordance with aspects of the present disclosure, at least one of the instruments 130 and 132 is configured to monitor a pressure within the vessel 100 distal of the stenosis 108 and at least one of the instruments 130 and 132 is configured to monitor a pressure within the vessel proximal of the stenosis. In that regard, the instruments 130, 132 are sized and shaped to allow positioning of the at least one element configured to monitor pressure within the vessel 100 to be positioned proximal and/or distal of the stenosis 108 as necessary based on the configuration of the devices. In that regard, FIG. 3 illustrates a position 138 suitable for measuring pressure distal of the stenosis 108. The position 138 is less than 5 cm, less than 3 cm, less than 2 cm, less than 1 cm, less than 5 mm, and/or less than 2.5 mm from the distal end of the stenosis 108 (as shown in FIG. 2) in some instances. FIG. 3 also illustrates a plurality of suitable positions for measuring pressure proximal of the stenosis 108. In that regard, positions 140, 142, 144, 146, and 148 each represent a position that is suitable for monitoring the pressure proximal of the stenosis in some instances. In that regard, the positions 140, 142, 144, 146, and 148 are positioned at varying distances from the proximal end of the stenosis 108 ranging from more than 20 cm down to about 5 mm or less. Generally, the proximal pressure measurement will be spaced from the proximal end of the stenosis. Accordingly, in some instances, the proximal pressure measurement is taken at a distance equal to or greater than an inner diameter of the lumen of the vessel from the proximal end of the stenosis. In the context of coronary artery pressure measurements, the proximal pressure measurement is generally taken at a position proximal of the stenosis and distal of the aorta, within a proximal portion of the vessel. However, in some particular instances of coronary artery pressure measurements, the proximal pressure measurement is taken from a location inside the aorta. In other instances, the proximal pressure measurement is taken at the root or ostium of the coronary artery. In some instances, the proximal pressure measurement is referred to as the aortic pressure.

Figure 4:
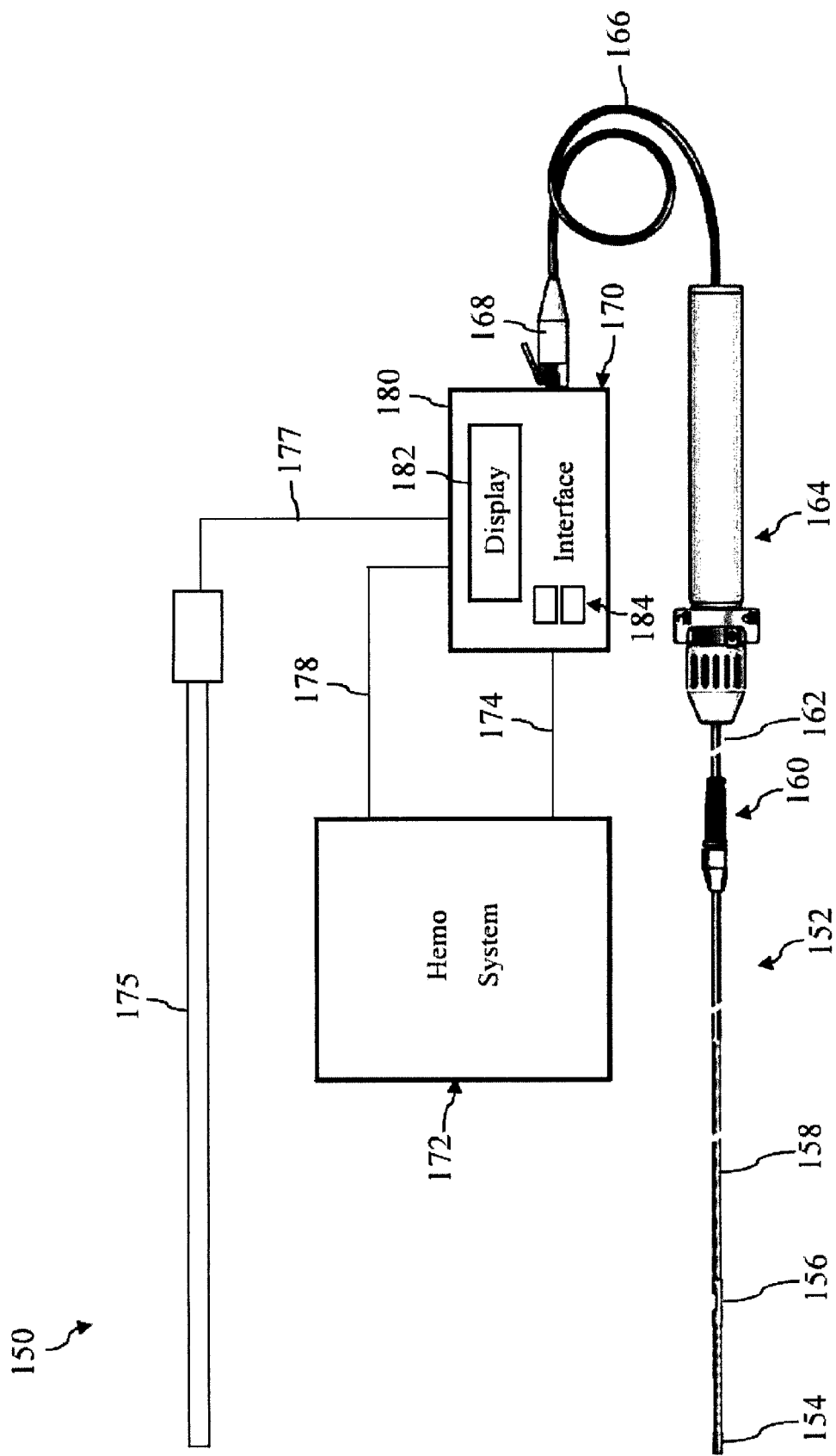
FIG. 4 is a diagrammatic, schematic view of a system according to an embodiment of the present disclosure.

Referring now to FIG. 4, shown therein is a system 150 according to an embodiment of the present disclosure. In that regard, FIG. 4 is a diagrammatic, schematic view of the system 150. As shown, the system 150 includes an instrument 152. In that regard, in some instances, instrument 152 is suitable for use as at least one of instruments 130 and 132 discussed above. Accordingly, in some instances the instrument 152 includes features similar to those discussed above with respect to instruments 130 and 132 in some instances.

In the illustrated embodiment, the instrument 152 is a guide wire having a distal portion 154 and a housing 156 positioned adjacent the distal portion. In that regard, the housing 156 is spaced approximately 3 cm from a distal tip of the instrument 152. The housing 156 is configured to house one or more sensors, transducers, and/or other monitoring elements configured to obtain the diagnostic information about the vessel. In the illustrated embodiment, the housing 156 contains at least a pressure sensor configured to monitor a pressure within a lumen in which the instrument 152 is positioned.

A shaft 158 extends proximally from the housing 156. A torque device 160 is positioned over and coupled to a proximal portion of the shaft 158. A proximal end portion 162 of the instrument 152 is coupled to a connector 164. A cable 166 extends from connector 164 to a connector 168. In some instances, connector 168 is configured to be plugged into an interface 170. In that regard, interface 170 is a patient interface module (PIM) in some instances, but in other instances it may be a hub that routes data signals to various systems and devices. In some instances, the cable 166 is replaced with a wireless connection. In that regard, the interface 170 includes an antenna for wireless data transmissions. It is understood that various communication pathways between the instrument 152 and the interface 170 may be utilized, including physical connections (including electrical, optical, and/or fluid connections), wireless connections, and/or combinations thereof.

The interface 170 is communicatively coupled to a medical measurement system, such as a hemodynamic system 172, via a connection 174. In some instances, the hemodynamic system 172 is a Siemens AXIOM Sensis, a Mennen Horizon XVu, or a Philips Xper IM Physiomonitoring 5. Together, connector 164, cable 166, connector 168, interface 170, and connection 174 facilitate communication between the one or more sensors, transducers, and/or other monitoring elements of the instrument 152 and the hemodynamic system 172. However, this communication pathway is exemplary in nature and should not be considered limiting in any way. In that regard, it is understood that any communication pathway between the instrument 152 and the interface 170 may be utilized, including physical connections (including electrical, optical, and/or fluid connections), wireless connections, and/or combinations thereof. In that regard, the hemodynamic system 172 includes an antenna for wireless data transmissions. Similarly, it is understood that any communication pathway between the interface 170 and the hemodynamic system 172 may be utilized, including physical connections (including electrical, optical, and/or fluid connections), wireless connections, and/or combinations thereof. Accordingly, it is understood that additional components (e.g., connectors, routers, switches, etc.) not illustrated in FIG. 4 may be included to facilitate communication between the instrument 152, the interface 170, and the hemodynamic system 172.

In some embodiments, the connection 174 is a wireless connection. In some instances, the connection 174 includes a communication link over a network (e.g., intranet, internet, telecommunications network, and/or other network). In that regard, it is understood that the hemodynamic system 172 is positioned remote from an operating area where the instrument 152 is being used in some instances. Having the connection 174 include a connection over a network can facilitate communication between the instrument 152 and the remote hemodynamic system 172 regardless of whether the hemodynamic system is in an adjacent room, an adjacent building, or in a different state/country. Further, it is understood that the communication pathway between the instrument 152 and the hemodynamic system 172 is a secure connection in some instances. Further still, it is understood that, in some instances, the data communicated over one or more portions of the communication pathway between the instrument 152 and the hemodynamic system 172 is encrypted.

The system 150 also includes an instrument 175. In that regard, in some instances instrument 175 is suitable for use as at least one of instruments 130 and 132 discussed above. Accordingly, in some instances the instrument 175 includes features similar to those discussed above with respect to instruments 130 and 132. In the illustrated embodiment, the instrument 175 is a catheter-type device. In that regard, the instrument 175 includes one or more sensors, transducers, and/or other monitoring elements adjacent a distal portion of the instrument configured to obtain the diagnostic information about the vessel. In the illustrated embodiment, the instrument 175 includes a pressure sensor configured to monitor a pressure within a lumen in which the instrument 175 is positioned. In one particular embodiment, instrument 175 is a pressure-sensing catheter that includes a fluid column extending along its length. In such an embodiment, a hemostasis valve is fluidly coupled to the fluid column of the catheter, a manifold is fluidly coupled to the hemostasis valve, and tubing extends between the components as necessary to fluidly couple the components. In that regard, the fluid column of the catheter is in fluid communication with a pressure sensor via the valve, manifold, and tubing. In some instances, the pressure sensor is part of or in communication with hemodynamic system 172. In other instances, the pressure sensor is a separate component positioned between the instrument 175 and the interface 170 or between the interface 170 and the hemodynamic system 172. The instrument 175 is in communication with the interface 170 via connection 177. The interface 170, in turn, is communicatively coupled to the computing device 172 via a connection 178.

Similar to the connections between instrument 152 and the interface 170 and the hemodynamic system 172, connections 177 and 178 facilitate communication between the one or more sensors, transducers, and/or other monitoring elements of the instrument 175 and the interface 170 and the hemodynamic system 172. Again, however, this communication pathway is exemplary in nature and should not be considered limiting in any way. In that regard, it is understood that any communication pathway between the instrument 175 and the interface 170 may be utilized, including physical connections (including electrical, optical, and/or fluid connections), wireless connections, and/or combinations thereof. Similarly, it is understood that any communication pathway between the interface 170 and the hemodynamic system 172 may be utilized, including physical connections (including electrical, optical, and/or fluid connections), wireless connections, and/or combinations thereof. Accordingly, it is understood that additional components (e.g., connectors, routers, switches, etc.) not illustrated in FIG. 4 may be included to facilitate communication between the instrument 175, the interface 170, and the hemodynamic system 172.

In some embodiments, the connection 178 is a wireless connection. In some instances, the connection 178 includes a communication link over a network (e.g., intranet, internet, telecommunications network, and/or other network). In that regard, it is understood that the hemodynamic system 172 is positioned remote from an operating area where the instrument 175 is being used in some instances. Having the connection 178 include a connection over a network can facilitate communication between the instrument 175 and the remote hemodynamic system 172 regardless of whether the computing device is in an adjacent room, an adjacent building, or in a different state/country. Further, it is understood that the communication pathway between the instrument 175 and the hemodynamic system 172 is a secure connection in some instances. Further still, it is understood that, in some instances, the data communicated over one or more portions of the communication pathway between the instrument 175 and the hemodynamic system 172 is encrypted.

It is understood that one or more components of the system 150 are not included, are implemented in a different arrangement/order, and/or are replaced with an alternative device/mechanism in other embodiments of the present disclosure. Alternatively, additional components and/or devices may be implemented into the system. Generally speaking, the communication pathway between either or both of the instruments 152, 175 and the hemodynamic system 172 may have no intermediate nodes (i.e., a direct connection), one intermediate node between the instrument and the computing device, or a plurality of intermediate nodes between the instrument and the computing device.

In some embodiments, the interface 170 includes a wireless transceiver and is configured to wirelessly transmit pressure readings from one or both of the instruments 152 and 175 to other devices in the system 150, such as a computing device 180. For example, the interface 170 may wirelessly transmit a distal pressure and/or distal pressure waveform, a proximal (i.e., aortic) pressure and/or proximal pressure waveform, to the computing device 180. In one embodiment, the computing device 180 is a computer system with the hardware and software to acquire, process, and display multi-modality medical data, but, in other embodiments, the computing device 180 may be any other type of computing system operable to process medical data. For example, in some instances the computing device 180 utilizes the distal pressure and/or distal pressure waveform with the proximal pressure and/or proximal pressure waveform to calculate FFR, calculate iFR, calculate a pressure differential between the proximal and distal pressures, identify a suitable diagnostic window for performing a pressure differential calculation without administering a hyperemic agent to the patient, calculate a pressure differential during the identified diagnostic window, calculate any other medical diagnostic characterization that is influenced by distal pressure and/or proximal (i.e., aortic) pressure, and any combinations thereof.

In the embodiments in which computing device 180 is a computer workstation, the system includes at least a processor such as a microcontroller or a dedicated central processing unit (CPU), a non-transitory computer-readable storage medium such as a hard drive, random access memory (RAM), and/or optical read only memory (CD-ROM, DVD-ROM, Blu-Ray), a video controller such as a graphics processing unit (GPU), and a network communication device such as an Ethernet controller or a wireless communication transceiver 182. In some instances, the computing device 180 is portable (e.g., handheld, on a rolling cart, etc.). Further, it is understood that in some instances computing device 180 comprises a plurality of computing devices. In some instances, the medical system 150 is deployed in a catheter lab having a control room, with the computing device 180 being located in the control room or the catheter lab itself. In other embodiments, the computing device 180 may be located elsewhere, such as in a centralized information technology area in a medical facility, or at an off-site location (i.e., in the cloud).

In some embodiments, the interface 170 itself includes a processor and random access memory and is programmed to execute steps associated with the data acquisition and analysis described herein. In particular, in some embodiments the interface 170 is configured to receive and display pressure readings from one or both of the instruments 152 and 175 and/or calculate (and display) FFR or other pressure differential based on the pressure measurements obtained from the instruments 152 and 175. Accordingly, it is understood that any steps related to data acquisition, data processing, instrument control, and/or other processing or control aspects of the present disclosure, including those incorporated by reference, may be implemented by the interface 170 using corresponding instructions stored on or in a non-transitory computer readable medium accessible by the computing device. In some embodiments, the interface 170 includes one or more processing and/or signal conditioning features and/or associated components/circuitry as described in U.S. Pat. No. 6,585,660, which is hereby incorporated by reference in its entirety.

In the embodiments in which the interface 170 includes a wireless transceiver and is also configured to calculate FFR, iFR, or another diagnostic characterization differential based on the pressure measurements obtained from the instruments 152 and 175, the interface 170 may first calculate the diagnostic characterization and then wirelessly transmit the pre-calculated result to one or more other devices such as the computing device 180 and/or hemodynamic system 172. In other embodiments, the hemodynamic system 172 itself may perform FFR, iFR, or other diagnostic characterization calculations.

In the illustrated embodiment of FIG. 4, the interface 170 includes a housing 184. The housing 184 contains the electronic components of the interface 170. In some embodiments, the interface 170 is sized to be handheld and/or sized to be positioned on or near a patient bed (e.g., attached to a bed rail or IV pole). In that regard, in some instances the interface 170 is similar in size to the SmartMap® Pressure Instrument available from Volcano Corporation, which has housing dimensions of approximately 15.75 cm (6.3") wide, 8.853 cm (3.54") tall, and 4.48 cm (1.79") deep. For example, the interface 170 may have a width between about 5 cm and about 25 cm, a height between about 5 cm and about 25 cm, and a depth between about 1 cm and about 10 cm. In some instances, the interface 170 also includes a display and one or more virtual or physical buttons configured to facilitate use of the interface. In some alternative embodiments, the interface 170 itself may be replaced by a circuitry-containing "smart" cable, or it may be completely obviated by circuitry that is implemented on the pressure guidewire 152 itself, for example in accordance with U.S. Provisional Patent Application No. 61/788,098, filed on Mar. 15, 2013, entitled "SMART INTERFACE CABLE FOR COUPLING A DIAGNOSTIC MEDICAL DEVICE WITH A MEDICAL MEASUREMENT SYSTEM", the disclosure of which is herein incorporated by reference in its entirety.

According to the various aspects of the present disclosure, one or more proprietary software or programs (e.g., FFR or iFR) from a given medical device manufacturer (hereinafter referred to as manufacturer X) is installed on the hemodynamic system 172 (or another suitable medical measurements system). Note that the hemodynamic system 172 may have a different manufacturer than manufacturer X. In other words, the entity manufacturing the hemodynamic system 172 may be a different entity than the one designing the one or more proprietary software programs. A diagnostic medical device such as the pressure wire 152 is coupled to the interface 170, which is then coupled to the hemodynamic system 172, for example through an aortic input of the hemodynamic system 172.

As the interface 170 is detected by the hemodynamic system 172, or alternatively when the FFR or iFR program is being activated, the software on the hemodynamic system 172 begins to monitor for a proprietary signal to come across the sense lines of the aortic input. In some embodiments, an operator would press a button on the interface 170, which allows the interface 170 to interrogate the pressure wire 152 regarding its manufacturing identity. For example, the interface 170 may electronically communicate with the pressure wire 152 through an EPROM of the pressure wire 152. In some alternative embodiments, the interface 170 need not necessarily communicate with the pressure wire 152 directly. For example, the hemodynamic system 172 that is connected to the interface 170 may communicate with the pressure wire 152 and verify that the wire has the correct manufacturing identity. In some embodiments, the pressure guide 152 contains a radio-frequency identification (RFID) chip. The manufacturing identity (or other types of identification information such as manufacturer site, expiration data, date of past use, etc.) may be extracted from the pressure guide 152 through communication with the RFID chip. In the present embodiment, based on the manufacturing identity supplied by the pressure wire 152, the interface 170 generates a proprietary signal and sends the proprietary signal to the hemodynamic system 172 for analysis. The interface 170 may send the proprietary signal in a recurring loop.

It is understood that the proprietary signal is sent through the channel (i.e., the sense lines of the aortic input) that is normally reserved to receive pressure wave data. The hemodynamic system 172 is "expecting" to see pressure wave data gathered by the pressure wire 152, but the software (developed by the manufacturer X) on the hemodynamic system 172 monitors the incoming signals to check for the proprietary signal. In this manner, the present disclosure involves sending artificial pressure data that contains a coded message.

Figures 5A, 5B, 5C, 5D:
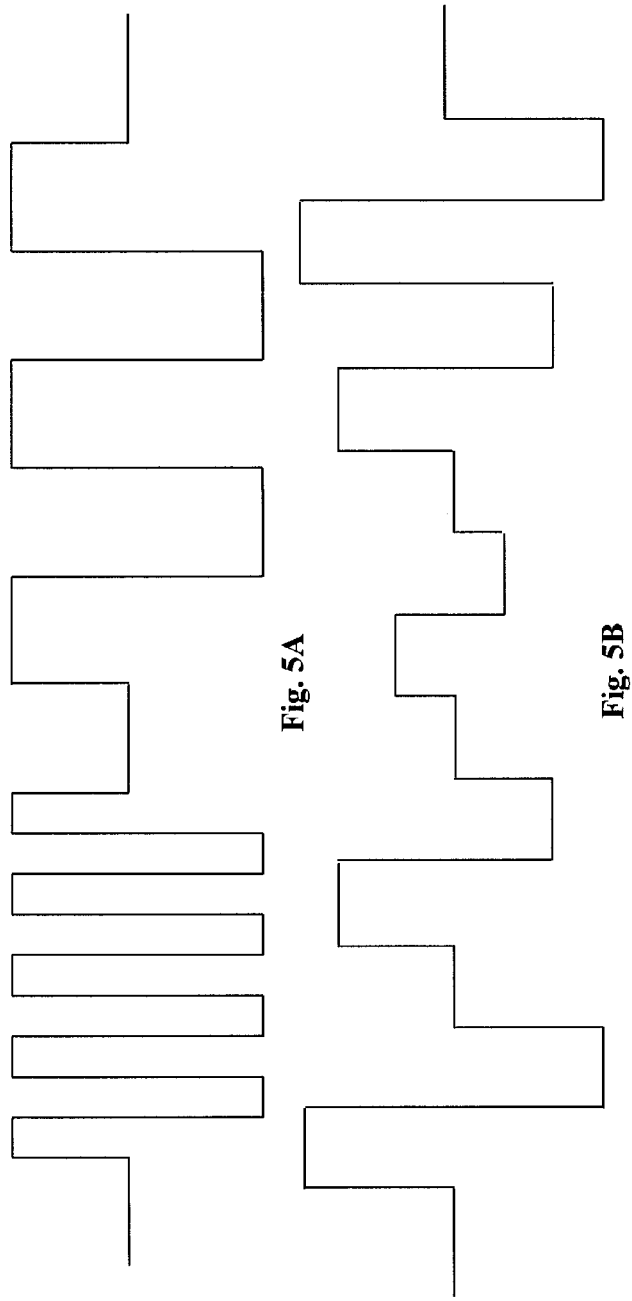
FIGS. 5A-5D are plots of example proprietary signals and example pressure data, respectively.

With reference now to FIGS. 5A-5B, there are many ways for the proprietary signal to be structured according to the various aspects of the present disclosure. In some embodiments, the proprietary signal may be a frequency modulated or frequency dependent signal in a unique pattern. In some other embodiments, the proprietary signal may be a pulse width modulated or pulse width dependent signal in a unique pattern. An example of a frequency dependent or pulse width dependent proprietary signal plotted over time is shown in FIG. 5A.

In other embodiments, the proprietary signal may be an amplitude modulated or amplitude dependent signal in a unique pattern. An example of an amplitude dependent proprietary signal plotted over time is shown in FIG. 5B.

In yet other embodiments, the proprietary signal may be a capacitive signal in a unique pattern. An example of a capacitive proprietary signal plotted over time is shown in FIG. 5C.

It is also understood that the proprietary signal may be a combination of a frequency modulated signal, a pulse width modulated signal, an amplitude modulated signal, or a capacitive signal. Regardless of the specific format, the proprietary signal is distinctly different from the typical pressure data (gathered by the pressure wire) that comes through the aortic input sense lines of the hemodynamic system 172. To demonstrate the differences between the proprietary signal and the typical pressure data that comes through the aortic input sense lines, FIG. 5D illustrates a graph of example pressure data plotted over time.

In certain embodiments, the proprietary signal may be structured such that certain pulses represent alpha numeric characters, thereby allowing for information from the pressure wire 152 (e.g., serial number, date of manufacturing, etc.) to be communicated from the programmable pressure wire EPROM to the hemodynamic system 172 via the aortic input sense lines. For example, the following table lists a conversion or correspondence between digits 0-9 and signals with certain frequencies.

| Digit | Signal Frequency |
|---|---|
| 0 | 3.0 Hz |
| 1 | 3.5 Hz |
| 2 | 4.0 Hz |
| 3 | 4.5 Hz |
| 4 | 5.0 Hz |
| 5 | 5.5 Hz |
| 6 | 6.0 Hz |
| 7 | 6.5 Hz |
| 8 | 7.0 Hz |
| 9 | 7.5 Hz |
| Start Signal | 8.0 Hz |
| Stop Signal | 8.5 Hz |

According to the table above, the software on the hemodynamic system 172 monitors for a proprietary signal. When a signal with 8.0 Hz frequency is received, the hemodynamic system 172 interprets this signal as the start of the proprietary signal transmission, which will contain the code that identifies a feature of the pressure wire 152 (e.g., the manufacturer of the pressure wire). Subsequently, distinct signal segments with unique frequencies (ranging from 3.0 Hz to 7.5 Hz in 0.5 Hz increments) are received by the hemodynamic system 172. There may be pauses or other suitable forms of division between these signal segments to help the software separately identify them. For example, if the following signal segments are received: 7.0 Hz, 5.0 Hz, 4.5 Hz, 6.5 Hz, 3.0 Hz, 6.0 Hz, the software will translate these signal segments into the following code 843706. Of course, this code may be any length, depending on the number of signal segments received. The code may also represent any number of things, for example the serial number of the pressure wire 152, a manufacturer part number of the pressure wire 152, etc.

When the software program detects the stop signal (the 8.5 Hz signal), it understands that the proprietary signal transmission is now over. The software on the hemodynamic system 172 then analyzes the received proprietary signal. For example, the software compares the translated code (based on the received proprietary signal) to a predefined code, which may already be pre-programmed into the software. In some instances, a correct (or expected) serial number of a pressure wire made by manufacturer X is pre-programmed into the software. Based on the received proprietary signal, if the software detects that the transmitted code matches with the pre-programmed serial number, the software knows that the pressure wire being used is made by an expected (or "correct") manufacturer. The software will then unlock the FFR or iFR programs (or other pressure wire derived parameters) for execution on the hemodynamic system 172. In other words, the FFR or iFR programs may be previously hidden or otherwise inaccessible to the operator. After the unlocking, however, the availability of the FFR or iFR programs may be made apparent to the operator. The operator may press a button on the interface 170 to stop sending the proprietary signal and start sending the pressure wire sensed pressure signal to the hemodynamic system 172.

Although not discussed in detail for reasons of simplicity, it is understood that the present disclosure also allows for an encryption protocol that would use information unique to each pressure wire in some embodiments. By doing so, the proprietary signal may be unique for each pressure wire 152 and therefore more difficult to crack or simulate. Alternatively, the proprietary signal could be based upon other data not related to the pressure wire 152, such as the current date or an unlock sequence manually entered by the operator.

One of the problems solved by the present disclosure is the prevention of the user of unauthorized diagnostic medical devices (e.g., pressure wires). Conventionally, there is no identification between a medical measurement system such as the hemodynamic system 172 and a remote diagnostic medical device such as the pressure wire 152. This means diagnostic medical devices from any manufacturer may be used with a medical measurement system with the ability to execute proprietary programs such as FFR or iFR. This poses a safety risk and increases liability for the manufacturer, since the manufacturer cannot ensure the accuracy or reliability of diagnostic medical devices made by someone else.

In comparison, according to the various aspects of the present disclosure, if a given manufacturer X wishes to prevent the use of diagnostic medical devices made by other manufacturers in conjunction with a hemodynamic system, it could configure the software installed on the hemodynamic system in a manner such that the proprietary programs such as FFR or iFR (or other parameters derived from the diagnostic medical device) will be made available only if a diagnostic medical device of the correct type and/or made by the manufacturer X is detected. In addition, the communication and identification scheme disclosed herein are accomplished without having to add or modify hardware on the hemodynamic system. In situations where necessary, only a software update on the hemodynamic system is needed. Furthermore, a proprietary signal that changes based on the date, a code entered into the interface, or some other predictable piece of data may further delay the compromising of the security method disclosed herein.

It is understood that in some embodiments, the unlocking discussed above may only apply to more sensitive (or more valuable) proprietary programs such as the iFR, whereas more generic programs such as FFR may be made available without the unlocking. Stated differently, the software residing on the hemodynamic system may decide which pressure wire derived parameters should be made readily available, and which other parameters should be unlocked only after the correct manufacturer identity has been confirmed.

Figure 6:
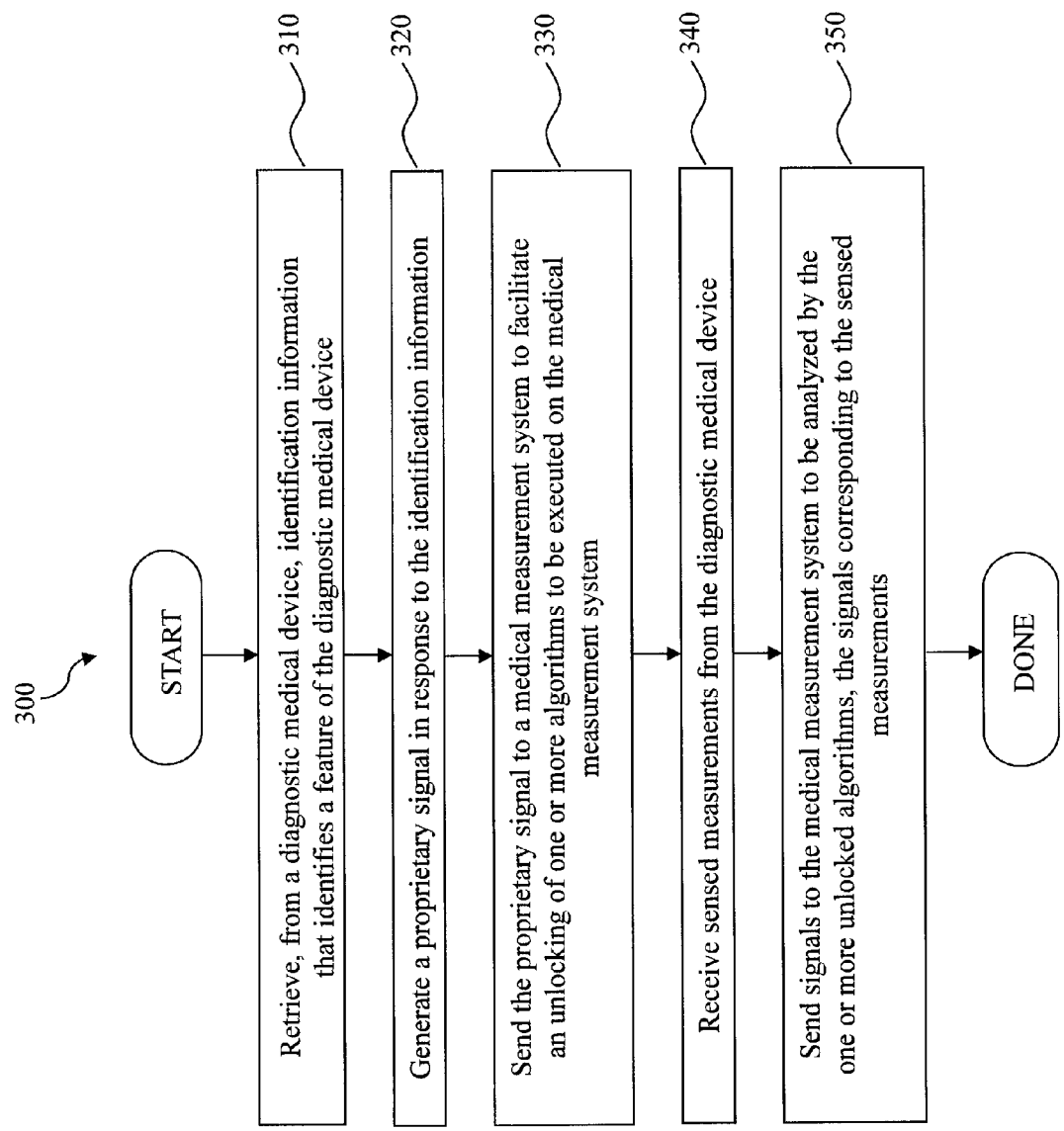
FIG. 6 is simplified flowchart illustrating a method according to an aspect of the present disclosure.

FIG. 6 is a simplified flowchart illustrating a method 300 according to one aspect of the present disclosure. In some embodiments, the method 300 is performed from the perspective of an electronic interface between a medical measurement system and a remote diagnostic medical device.

The method 300 includes a step 310, in which identification information is retrieved from the diagnostic medical device. The identification information identifies a feature of the diagnostic medical device. In certain embodiments, the feature includes manufacturing information of the diagnostic medical device. For example, the manufacturing information may include an identity of the manufacturer of the diagnostic medical device. As other examples, the manufacturing information may include a manufacture site of the diagnostic medical device, expiration data of the diagnostic medical device, and date of past use of the diagnostic medical device. In some embodiments, the diagnostic medical device includes a pressure guide wire.

The method 300 includes a step 320, in which a proprietary signal is generated in response to the identification information.

The method 300 includes a step 330, in which the proprietary signal is sent to a medical measurement system to facilitate an unlocking of one or more programs to be executed on the medical measurement system. In some embodiments, the medical measurement system includes a hemodynamic system.

The method 300 includes a step 340, in which sensed measurements are received from the diagnostic medical device. In some embodiments, the sensed measurements include blood pressure measurements.

The method 300 includes a step 350, in which signals are sent to the medical measurement system to be analyzed by the one or more unlocked programs. The signals correspond to the sensed measurements. In some embodiments, the one or more unlocked programs include an instantaneous wave-free ratio (iFR) calculation based on the blood pressure measurements.

Figure 7:
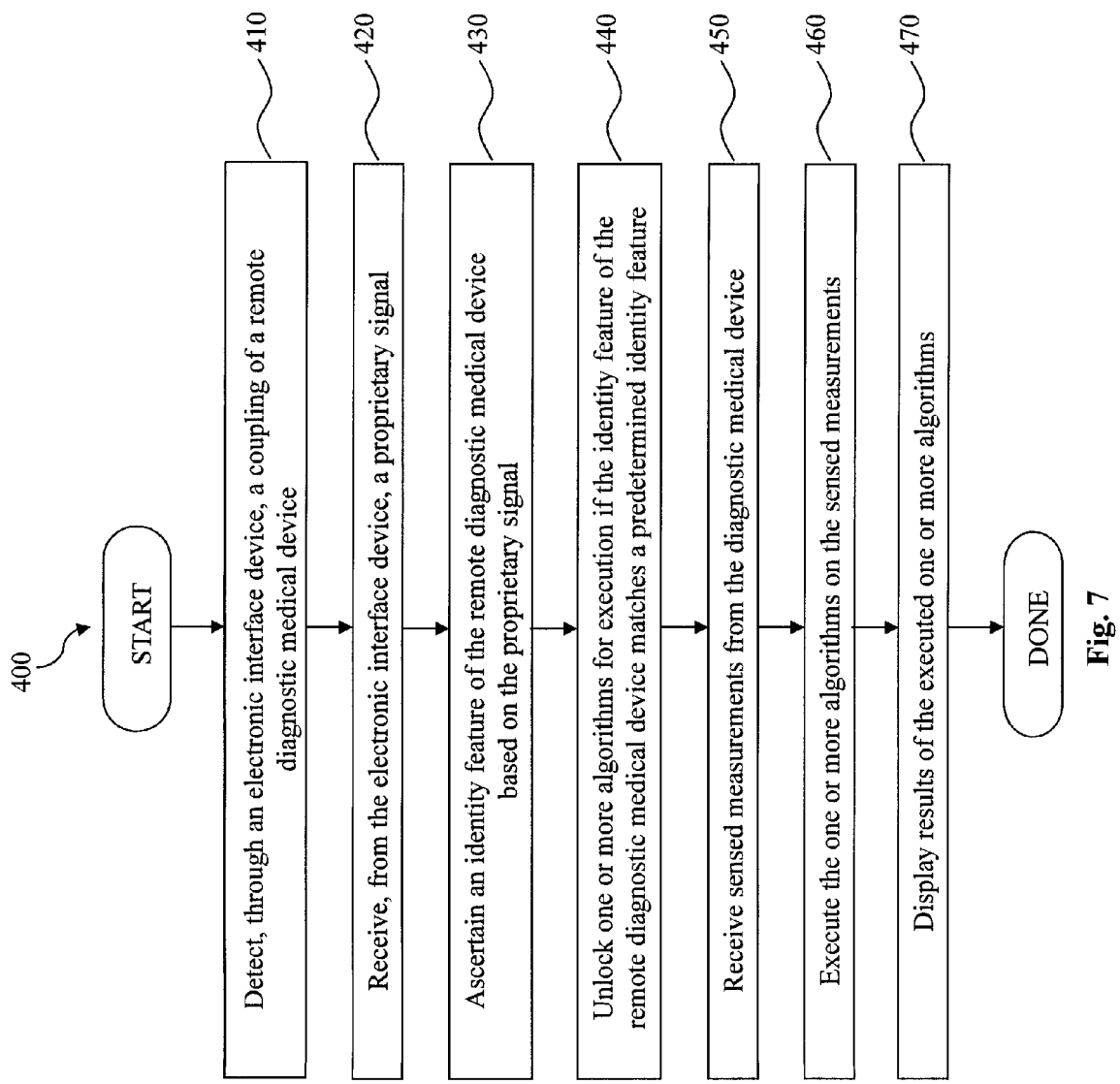
FIG. 7 is simplified flowchart illustrating a method according to an aspect of the present disclosure.

FIG. 7 is a simplified flowchart illustrating a method 400 according to another aspect of the present disclosure. In some embodiments, the method 400 is performed from the perspective of a medical measurement system, such as a hemodynamic system.

The method 400 includes a step 410, in which a coupling of a remote diagnostic medical device is detected through an electronic interface device. In some embodiments, the diagnostic medical device includes a pressure guide wire, and the electronic interface device is a device coupled between the pressure guide wire and the hemodynamic system.

The method 400 includes a step 420, in which a proprietary signal is received from the electronic interface device.

The method 400 includes a step 430, in which an identity feature of the remote diagnostic medical device is ascertained based on the proprietary signal. In some embodiments, the identity feature includes the type of diagnostic sensor, an identity of a manufacturer of the diagnostic medical device, a manufacture site of the diagnostic medical device, expiration data of the diagnostic medical device, or date of past use of the diagnostic medical device.

The method 400 includes a step 440, in which one or more programs is unlocked for execution if the identity feature of the remote diagnostic medical device matches a predetermined identity feature.

The method 400 includes a step 450, in which sensed measurements are received from the diagnostic medical device. In some embodiments, the sensed measurements include blood pressure measurements.

The method 400 includes a step 460, in which the one or more programs is executed on the sensed measurements. In some embodiments, the one or more programs include an instantaneous wave-free ratio (iFR) calculation based on the blood pressure measurements.

The method 400 includes a step 470, in which results of the executed one or more programs are displayed. In some embodiments, the results of the executed one or more programs are stored.

It is understood that the method 400 may be modified to accommodate process flows from slightly different point views. For example, in some embodiments, the availability of proprietary programs such as FFR or iFR are not hidden to an operator or a user. The operator may see the availability of these proprietary programs on the medical measurement system, for example as one or more graphical icons. The operator may attempt to execute a proprietary program by performing an interactive operation with the medical measurement system, for example clicking on one of the graphical icons. The interactive operation triggers an electronic message to be sent to the electronic interface device to verify that a proper or "correct" diagnostic medical device is attached. If the proper diagnostic medical device is attached, the proprietary program selected by the operator may be executed. If not, the medical measurement system may report back to the operator that the proprietary program cannot be executed due to an incompatible diagnostic medical device (or a similar message). The medical measurement system may also prompt the operator to replace the "improper" diagnostic medical device currently used with a "proper" diagnostic medical device from the correct manufacturer. In this process flow, the selection of a protected feature (e.g., FFR or iFR) triggers the check and verification of a remote diagnostic medical device.

Figure 8:
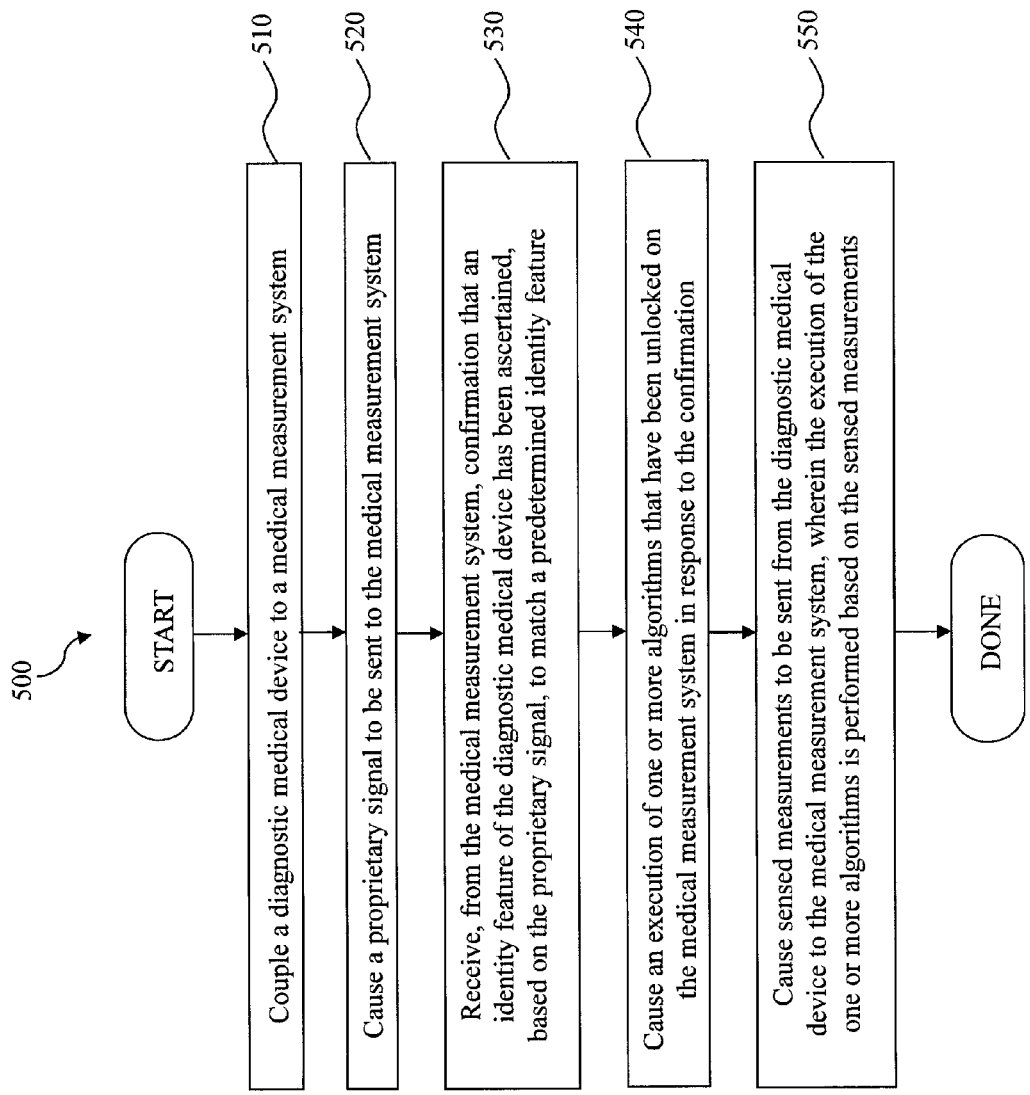
FIG. 8 is simplified flowchart illustrating a method according to an aspect of the present disclosure.

FIG. 8 is a simplified flowchart illustrating a method 500 according to yet another aspect of the present disclosure. In some embodiments, the method 500 is performed from the perspective of an operator in a medical measurement environment.

The method 500 includes a step 510, in which a diagnostic medical device is coupled to a medical measurement system. The coupling is performed such that the diagnostic medical device and the medical measurement system are coupled together through an electronic interface device. In some embodiments, the diagnostic medical device includes a pressure guide wire, and the medical measurement system includes a hemodynamic system.

The method 500 includes a step 520, in which a proprietary signal is caused to be sent to the medical measurement system. In some embodiments, this step may be triggered by the operator selecting a "protected" feature on the medical measurement system, as discussed above with reference to the alternative process flow in FIG. 7.

The method 500 includes a step 530, in which a confirmation is received from the medical measurement system. The confirmation confirms that an identity feature of the diagnostic medical device has been ascertained, based on the proprietary signal, to match a predetermined identity feature. In some embodiments, the identity feature includes an identity of a manufacturer of the diagnostic medical device, a manufacture site of the diagnostic medical device, expiration data of the diagnostic medical device, or date of past use of the diagnostic medical device.

The method 500 includes a step 540, in which an execution of one or more programs is caused. The one or more programs have been unlocked on the medical measurement system in response to the confirmation.

The method 500 includes a step 550, in which sensed measurements are caused to be sent from the diagnostic medical device to the medical measurement system. The execution of the one or more programs is performed based on the sensed measurements. In some embodiments, the sensed measurements include blood pressure measurements, and the one or more programs include an instantaneous wave-free ratio (iFR) calculation based on the blood pressure measurements.

Figure 9:
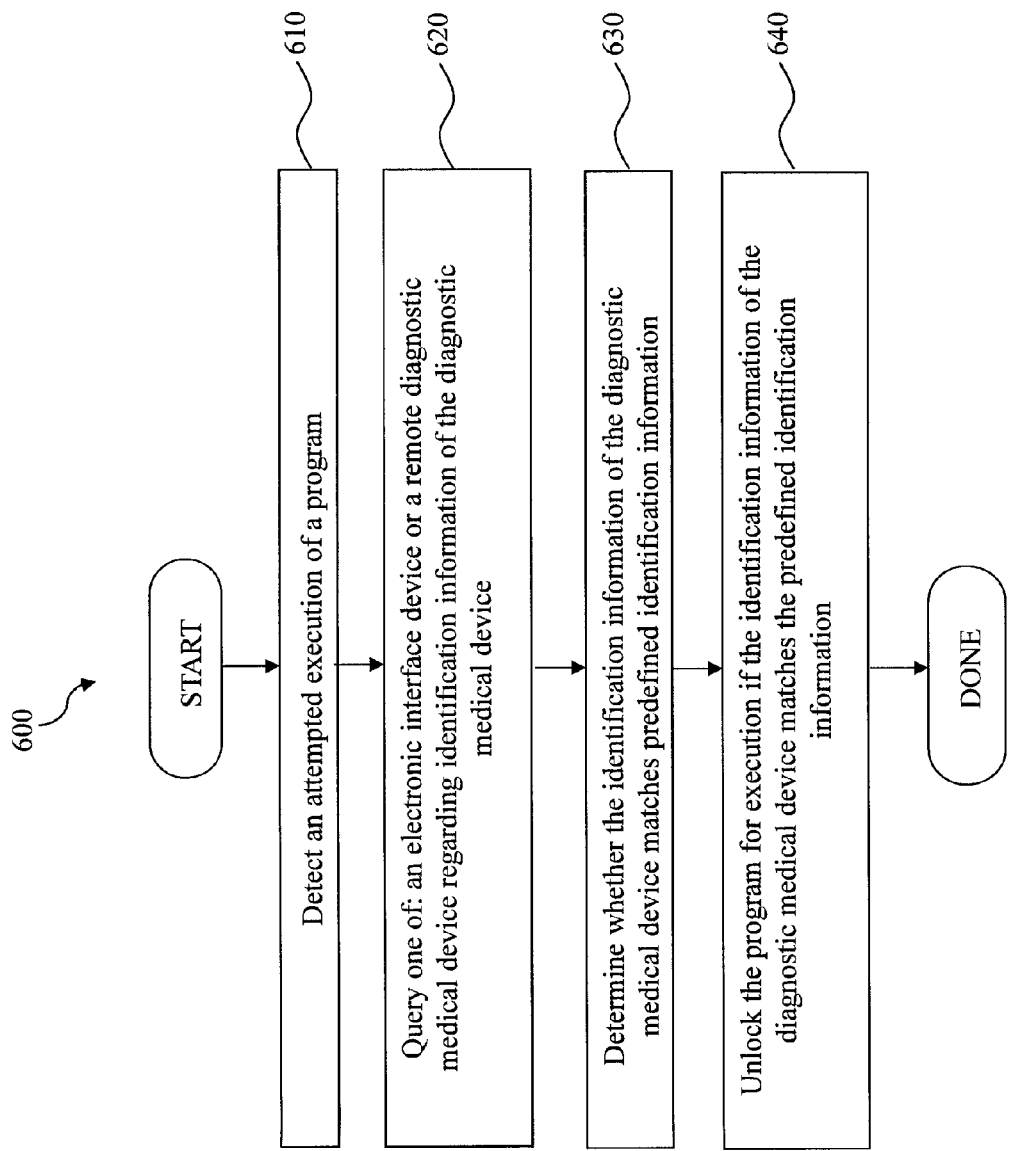
FIG. 9 is simplified flowchart illustrating a method according to an aspect of the present disclosure.

FIG. 9 is a simplified flowchart illustrating a method 600 according to another aspect of the present disclosure. In some embodiments, the method 600 is performed from the perspective of a medical measurement system, such as a hemodynamic system, but the method 600 is triggered by a user or operator's attempt to execute a proprietary program.

The method 600 includes a step 610, in which an attempted execution of a program is detected. In some embodiments, the program includes a fractional flow reserve (FFR) calculation or an instantaneous wave-free ratio (iFR) calculation.

The method 600 includes a step 620, in which a query regarding the identification information of the diagnostic medical device is made. The query is mad through one of: an electronic interface device or a remote diagnostic medical device. In other words, the query may be made through the electronic interface device coupled between the diagnostic medical device and the medical measurement system, or to the diagnostic medical device directly. In some embodiments, the query in step 620 is made through a wired connection. In other embodiments, the query in step 620 is made through a wireless connection. In some embodiments, the diagnostic medical device includes an RFID chip, and the query is made via communication with the RFID chip.

The method 600 includes a step 630, in which it is determined whether the identification information of the diagnostic medical device matches predefined identification information. In some embodiments, the identification information includes a type of the diagnostic medical device, an identity of the manufacturer of the diagnostic medical device, a manufacture site of the diagnostic medical device, expiration data of the diagnostic medical device, and date of past use of the diagnostic medical device.

The method 600 includes a step 640, in which the program is unlocked for execution if the identification information of the diagnostic medical device matches the predefined identification information.

It is understood that, although FFR and iFR are used as example proprietary programs to illustrate the various aspects of the present disclosure, the present disclosure is not limited to FFR or iFR. Still further, while a hemodynamic system is illustrated as the medical measurement system, the present disclosure is not limited thereto. The concepts discussed in the present disclosure may apply to any type of diagnostic medical device or medical measurement system including any of a variety of processing algorithms or software programs.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A method of authorizing a medical device for use, the method comprising:
   retrieving, by an electronic interface device, identification information from a diagnostic medical device that identifies a feature of the diagnostic medical device, the diagnostic medical device being configured to obtain pressure data within a vessel of a patient;
   generating, by the electronic interface device, a proprietary signal based on the identification information; and
   sending, from the electronic interface device, the proprietary signal through a channel configured to receive pressure data to a medical measurement system to facilitate an unlocking of one or more programs to be executed on the medical measurement system.

2. The method of claim 1, wherein:
   the diagnostic medical device includes a pressure guide wire; and
   the medical measurement system includes a hemodynamic system.

3. The method of claim 1, wherein the feature includes manufacturing information of the diagnostic medical device.

4. The method of claim 3, wherein the manufacturing information includes a type of the diagnostic medical device, an identity of the manufacturer of the diagnostic medical device, a manufacture site of the diagnostic medical device, expiration data of the diagnostic medical device, and date of past use of the diagnostic medical device.

5. The method of claim 1, further comprising:
   receiving pressure data from the diagnostic medical device; and
   sending the pressure wave data through the channel to the medical measurement system to be analyzed by the one or more unlocked programs.

6. The method of claim 5, wherein the pressure data includes blood pressure data.

7. The method of claim 5, wherein the one or more unlocked programs include a fractional flow reserve (FFR) calculation or an instantaneous wave-free ratio (iFR) calculation based on the pressure data.

8. A system, comprising:
   a diagnostic medical device configured to obtain pressure data within a vessel of a patient and containing identification information that identifies a feature of the diagnostic medical device; and
   an electronic interface device configured to serve as an interface between the diagnostic medical device and a medical measurement system, and is further configured to:
   receive the identification information from the diagnostic medical device,
   generate a proprietary signal based on the identification information, and
   send, through a channel configured to receive pressure wave data, the proprietary signal to the medical measurement system to facilitate unlocking of one or more executable programs on the medical measurement system based on the proprietary signal.

9. The system of claim 8, wherein the one or more programs is unlocked if the feature of the diagnostic medical device matches a predetermined feature.

10. The system of claim 8, wherein the feature includes manufacturing information of the diagnostic medical device.

11. The system of claim 10, wherein the manufacturing information includes a type of the diagnostic medical device or an identity of the manufacturer of the diagnostic medical device.

12. The system of claim 8, wherein:
   the diagnostic medical device includes a pressure guide wire; and
   the medical measurement system includes a hemodynamic system.

13. The system of claim 8, wherein:
   the electronic interface device is configured to send pressure data to the medical measurement system to be analyzed by the one or more unlocked programs.

14. The system of claim 13, wherein the pressure data includes blood pressure data.

15. The system of claim 13, wherein the one or more programs include a fractional flow reserve (FFR) calculation or an instantaneous wave-free ratio (iFR) calculation based on the blood pressure data.

16. A method, comprising:
   detecting an attempted execution of a program stored on a non-transitory, computer-readable storage medium and configured to be executed by a processor;
   querying one of: an electronic interface device or a diagnostic medical device regarding identification information of the diagnostic medical device, the diagnostic medical device being configured to obtain pressure data within a vessel of a patient;
   receiving, through a channel configured to receive pressure data, a proprietary signal generated based on the identification information;
   determining, based on the proprietary signal, that the diagnostic medical device is authorized; and
   unlocking the program for execution in response to determining that the diagnostic medical device is authorized.

17. The method of claim 16, wherein the detecting, the querying, the determining, and the unlocking are performed at least in part by a medical measurement system coupled to the diagnostic medical device through the electronic interface device.

18. The method of claim 16, wherein the querying is performed using a wired connection.

19. The method of claim 16, wherein the querying is performed wirelessly.

20. The method of claim 19, wherein the diagnostic medical device contains a radio-frequency identification (RFID) chip, and wherein the querying is performed through the RFID chip.

21. The method of claim 16, wherein:
   the diagnostic medical device includes a pressure guide wire; and
   the medical measurement system includes a hemodynamic system.

22. The method of claim 16, wherein the identification information includes a type of the diagnostic medical device, an identity of the manufacturer of the diagnostic medical device, a manufacture site of the diagnostic medical device, expiration data of the diagnostic medical device, and date of past use of the diagnostic medical device.

23. The system of claim 16, wherein the program includes a fractional flow reserve (FFR) calculation or an instantaneous wave-free ratio (iFR) calculation.

* * * * *